United States Patent
Dees, Jr.

(10) Patent No.: US 9,649,205 B2
(45) Date of Patent: *May 16, 2017

(54) DISTAL FEMORAL TRIAL WITH REMOVABLE CUTTING GUIDE

(71) Applicant: Smith & Nephew, Inc., Memphis, TN (US)

(72) Inventor: Roger Ryan Dees, Jr., Senatobia, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/725,693

(22) Filed: May 29, 2015

(65) Prior Publication Data

US 2015/0257900 A1    Sep. 17, 2015

Related U.S. Application Data

(60) Continuation of application No. 14/317,048, filed on Jun. 27, 2014, now Pat. No. 9,044,249, which is a continuation of application No. 13/101,609, filed on May 5, 2011, now Pat. No. 8,764,759, which is a
(Continued)

(51) Int. Cl.
| | |
|---|---|
| *A61B 17/58* | (2006.01) |
| *A61F 2/46* | (2006.01) |
| *A61B 17/16* | (2006.01) |
| *A61B 17/17* | (2006.01) |
| *A61B 17/15* | (2006.01) |

(Continued)

(52) U.S. Cl.
CPC .......... *A61F 2/4684* (2013.01); *A61B 17/155* (2013.01); *A61B 17/1675* (2013.01); *A61B 17/1764* (2013.01); *A61F 2/3859* (2013.01); *A61B 2017/1602* (2013.01); *A61B 2090/034* (2016.02); *A61F 2002/3863* (2013.01)

(58) Field of Classification Search
CPC combination set(s) only.
See application file for complete search history.

(56) References Cited

U.S. PATENT DOCUMENTS

| | | |
|---|---|---|
| 3,829,904 A | 8/1974 | Ling et al. |
| 4,337,773 A | 7/1982 | Raftopoulos et al. |
| 4,404,692 A | 9/1983 | Eftekhar |

(Continued)

FOREIGN PATENT DOCUMENTS

| | | |
|---|---|---|
| EP | 556997 A1 | 8/1993 |
| FR | 2742037 A1 | 6/1997 |

(Continued)

OTHER PUBLICATIONS

Notice of Reasons for Rejection for Japanese Application No. 2007-548480, mailed May 31, 2011.
(Continued)

*Primary Examiner* — Jan Christopher Merene
(74) *Attorney, Agent, or Firm* — Fish & Richardson P.C.

(57) ABSTRACT

Various embodiments of the present invention provide a distal femoral trial that allows a surgeon to cut the central box geometry of a distal femur using an implant-shaped trial. The trial includes a cutting guide that is removable from the trial and adjustable with respect to the trial. The guide is intended to control the depth and direction of the cutting instruments used to prepare the femur for a posterior stabilized implant.

42 Claims, 6 Drawing Sheets

Related U.S. Application Data division of application No. 11/316,255, filed on Dec. 21, 2005, now Pat. No. 7,963,968.

(60) Provisional application No. 60/638,185, filed on Dec. 21, 2004.

(51) Int. Cl.
*A61F 2/38* (2006.01)
*A61B 90/00* (2016.01)

(56) References Cited

U.S. PATENT DOCUMENTS

| | | |
|---|---|---|
| D273,894 S | 5/1984 | Kenna |
| D273,895 S | 5/1984 | Kenna |
| D274,090 S | 5/1984 | Kenna |
| D274,091 S | 5/1984 | Kenna |
| D274,092 S | 5/1984 | Kenna |
| D274,093 S | 5/1984 | Kenna |
| D274,094 S | 5/1984 | Kenna |
| D274,095 S | 5/1984 | Kenna |
| D274,161 S | 6/1984 | Kenna |
| D274,162 S | 6/1984 | Kenna |
| 4,550,448 A | 11/1985 | Kenna |
| 4,646,729 A | 3/1987 | Kenna et al. |
| 4,653,488 A | 3/1987 | Kenna |
| 4,668,290 A | 5/1987 | Wang et al. |
| 4,714,468 A | 12/1987 | Wang et al. |
| 4,721,104 A | 1/1988 | Kaufman et al. |
| 4,722,330 A | 2/1988 | Russell et al. |
| 4,787,383 A | 11/1988 | Kenna |
| 4,791,919 A | 12/1988 | Elloy et al. |
| 4,825,857 A | 5/1989 | Kenna |
| 4,834,756 A | 5/1989 | Kenna |
| 4,922,898 A | 5/1990 | Dunn |
| 4,926,847 A | 5/1990 | Luckman |
| 4,944,756 A | 7/1990 | Kenna |
| 5,002,581 A | 3/1991 | Paxson et al. |
| 5,035,700 A | 7/1991 | Kenna |
| 5,059,196 A | 10/1991 | Coates |
| 5,098,436 A | 3/1992 | Ferrante et al. |
| 5,100,409 A | 3/1992 | Coates et al. |
| 5,122,145 A | 6/1992 | Fishbane |
| 5,171,324 A | 12/1992 | Campana et al. |
| 5,176,684 A | 1/1993 | Ferrante et al. |
| 5,192,324 A | 3/1993 | Kenna |
| 5,258,032 A | 11/1993 | Bertin |
| 5,275,603 A | 1/1994 | Ferrante et al. |
| 5,340,362 A | 8/1994 | Carbone |
| 5,342,362 A | 8/1994 | Kenyon et al. |
| 5,344,423 A | 9/1994 | Dietz et al. |
| 5,344,461 A | 9/1994 | Phlipot |
| 5,358,524 A | 10/1994 | Richelsoph |
| 5,364,401 A | 11/1994 | Ferrante et al. |
| 5,441,537 A | 8/1995 | Kenna |
| 5,445,642 A | 8/1995 | McNulty et al. |
| 5,458,645 A | 10/1995 | Bertin |
| 5,462,550 A | 10/1995 | Dietz et al. |
| 5,486,178 A | 1/1996 | Hodge |
| 5,514,139 A | 5/1996 | Goldstein et al. |
| 5,542,947 A | 8/1996 | Treacy |
| 5,549,687 A | 8/1996 | Coates et al. |
| 5,554,158 A | 9/1996 | Vinciguerra et al. |
| 5,569,259 A | 10/1996 | Ferrante et al. |
| 5,624,444 A | 4/1997 | Wixon et al. |
| 5,634,927 A | 6/1997 | Houston et al. |
| 5,653,714 A | 8/1997 | Dietz et al. |
| 5,662,656 A | 9/1997 | White |
| 5,683,397 A | 11/1997 | Vendrely et al. |
| 5,702,460 A | 12/1997 | Carls et al. |
| 5,709,689 A | 1/1998 | Ferrante et al. |
| 5,716,361 A | 2/1998 | Masini |
| 5,720,752 A | 2/1998 | Elliott et al. |
| 5,743,915 A | 4/1998 | Bertin et al. |
| 5,769,854 A | 6/1998 | Bastian et al. |
| 5,769,855 A | 6/1998 | Bertin et al. |
| 5,776,201 A | 7/1998 | Colleran et al. |
| 5,810,829 A | 9/1998 | Elliott et al. |
| 5,810,831 A | 9/1998 | D'Antonio |
| 5,860,980 A | 1/1999 | Axelson, Jr. et al. |
| 5,879,393 A | 3/1999 | Whiteside et al. |
| 5,885,296 A | 3/1999 | Masini |
| 5,897,559 A | 4/1999 | Masini |
| 5,935,132 A | 8/1999 | Bettuchi et al. |
| 5,944,722 A | 8/1999 | Masini |
| 5,957,926 A | 9/1999 | Masini |
| 6,013,081 A | 1/2000 | Burkinshaw et al. |
| 6,056,756 A | 5/2000 | Eng et al. |
| 6,071,311 A | 6/2000 | O'Neil et al. |
| 6,077,269 A | 6/2000 | Masini |
| 6,077,270 A | 6/2000 | Katz |
| 6,102,916 A | 8/2000 | Masini |
| 6,187,010 B1 | 2/2001 | Masini |
| 6,217,618 B1 | 4/2001 | Hileman |
| 6,290,704 B1 | 9/2001 | Burkinshaw et al. |
| 6,458,135 B1 | 10/2002 | Harwin et al. |
| 6,488,687 B1 | 12/2002 | Masini |
| 6,500,179 B1 | 12/2002 | Masini |
| 6,503,254 B2 | 1/2003 | Masini |
| 6,558,391 B2 | 5/2003 | Axelson, Jr. et al. |
| 6,575,980 B1 | 6/2003 | Robie et al. |
| 6,629,999 B1 | 10/2003 | Serafin, Jr. |
| 6,740,092 B2 | 5/2004 | Lombardo et al. |
| 6,783,551 B1 | 8/2004 | Metzger et al. |
| 6,827,739 B2 | 12/2004 | Griner et al. |
| 7,674,268 B2 | 3/2010 | Cuckler et al. |
| 7,729,478 B1 | 6/2010 | Coughlan et al. |
| 2001/0001120 A1 | 5/2001 | Masini |
| 2002/0107522 A1 | 8/2002 | Picard et al. |
| 2003/0028196 A1 | 2/2003 | Bonutti |
| 2004/0039450 A1 | 2/2004 | Griner et al. |
| 2004/0078043 A1 | 4/2004 | Masini |
| 2004/0153087 A1 | 8/2004 | Sanford et al. |
| 2004/0260301 A1 | 12/2004 | Lionberger et al. |
| 2005/0055028 A1 | 3/2005 | Haines |
| 2005/0080424 A1 | 4/2005 | Cuckler et al. |
| 2005/0149040 A1 | 7/2005 | Haines et al. |
| 2009/0088762 A1 | 4/2009 | Koenemann |

FOREIGN PATENT DOCUMENTS

| | | |
|---|---|---|
| WO | WO9533414 A1 | 12/1995 |
| WO | WO9730640 A1 | 8/1997 |
| WO | WO9730648 A1 | 8/1997 |
| WO | WO9832384 A1 | 7/1998 |
| WO | WO9852499 A1 | 11/1998 |
| WO | WO9920192 A1 | 4/1999 |
| WO | WO0013594 A1 | 3/2000 |
| WO | WO2008054389 A1 | 5/2008 |

OTHER PUBLICATIONS

Communication Pursuant to Article 94(3) EPC for European Application No. 05855250.6, mailed Feb. 3, 2011.
Office Action for Canadian Application No. 2,591,977, mailed Feb. 14, 2012.
Examiner's First Report on Australian Patent Application No. 20053191939, mailed Jul. 14, 2010.
International Search Report in related International Application No. PCT/US2005/046658.
International Search Report in related International Application No. PCT/US2006/042705.
T-1™ Instrumentation, 01 page undated.
Brochure entitled 'Ascent™ Total Knee System Anterior Referencing Surgical Technique,' Surgical Technique by Rick Basset, M.D. and Michael Jacobs, M.D., Taking total knee replacement to new heights, Biomet Orthopedics, Inc., 28 pages (2000).
Brochure entitled 'Monogram® Knee Instruments,' Stryker Howmedica Osteonics, Monogram® IM Revision Instrument Surgical Technique with Offsetting Instruments Total Stabilizer, 32 pages (1999).

(56) References Cited

OTHER PUBLICATIONS

Brochure entitled 'NexGen® System Complete Knee Solution,' LCCK NexGen® Complete Knee Solution Revision Instrumentation Surgical Technique for Legacy® Knee Constrained Condylar Knee, Zimmer, 60 pages (2001).
Biomet Orthopedics, Inc.—Maxim Complete Knee System Primary I Posterior Stabilized Surgical Technique (see Posterior Stabilized Intercondylar Box Resection and Size Specific Posterior Stabilized Intercondylar Box Resection sections) © 1994.
Biomet Orthopedics, Inc.—Maxim Complete Knee System Constrained Surgical Technique (see Intercondylar Box Resection) © 1995.
Biomet, Inc.—Maxim the Complete Knee System © 1995.
Biomet Orthopedics, Inc. AGC Total Knee System Tradition Series © 1995.
Lombardi, et al., 'Intercondylar Distal Femoral Fracture. An Unreported Complication of Posterior-Stabilized Total Knee Arthroplasty,' J. Arthroplasty, 10(5):643-650 (1995).
Insall, et al., 'Current Concepts in Primary and Revision Total Knee Arthroplasty' Bristol-Myers SquibbiZimmer Orthopaedic Symposium Bristol-Myers Squibbi Zimmer Orthopaedic Symposium Series, p. 204 Medical, 1996, 286 pages.
Thomas P. Sculco, M.D., Surgical Treatment of Rheumatoid Arthritis, p. 260, 1992, Mosby Year Book.
Reconstructive Surgery of the Joints, Second Edition, vol. 2, p. 1414, Edited by Bernard F. Morrey, M.D., Professor of Orthopedics, Mayo Medical School, 1996, Churchill Livingston.
Examiner's first report dated Jul. 14, 2010 issued in relatedAustralian Patent Application No. 200 5319139.
Office Communication dated Feb. 3, 2011 in related European Patent Application No. 05855250.6.
Communication Pursuant to Article 94(3) EPC in related European Application No. 06836779.6 mailed Feb. 25, 2013.
Communication Pursuant to Article 94(3) EPC in related European Application No. 05855250.6 mailed Dec. 3, 2015, 6 pages.
Communication Pursuant to Article 94(3) EPC issued in EP Application No. 05855250.6, Dec. 23, 2016.

DISTAL FEMORAL TRIAL WITH REMOVABLE CUTTING GUIDE

CROSS-REFERENCE TO RELATED APPLICATIONS

This application is a continuation of U.S. patent application Ser. No. 14/317,048, filed Jun. 27, 2014, now U.S. Pat. No. 9,044,249, issued Jun. 2, 2015, which is a continuation of U.S. patent application Ser. No. 13/101,609, filed May 5, 2011, now U.S. Pat. No. 8,764,759, issued Jul. 1, 2014, which is a divisional of U.S. patent application Ser. No. 11/316,255, filed Dec. 21, 2005, now U.S. Pat. No. 7,963,968, issued Jun. 21, 2011, which claims benefit of U.S. Patent Application Ser. No. 60/638,185 filed Dec. 21, 2004 titled Distal-Femoral Prosthetic Trial and Resection Guide. The entire contents of the prior applications are hereby incorporated by reference herein.

FIELD OF THE INVENTION

The present invention relates generally to surgical orthopaedic trials and methods, particularly to trials and methods for preparing the distal femur of a patient to receive a femoral prosthesis.

BACKGROUND

Patients suffering from unstable, painful knee joints where the instability is caused by the lack or insufficiency of the posterior cruciate ligament may be candidates for a total knee arthroplasty using a posterior-stabilized knee prosthesis. Such an implant or prosthesis includes a tibial component, a femoral component, and typically, a mobile bearing insert (a patella component).

The tibial component is secured to a resected portion of the patient's tibia. This component has a post that receives a bearing or patella component. The femoral component typically has inner intersecting flat surfaces that interface with a surgically prepared distal femoral surface, and an outer surface with a curvature that faces the corresponding tibial component attached to the patient's tibia. The femoral component has two condylar regions with an intercondylar stabilizing housing that accepts the tibial post. These posterior stabilized and constrained femoral implant components have a cam housing in between the condyles of the femur (or the condylar regions).

Bone from the distal femur must be removed from this area to accommodate for this type of cam housing. This may be referred to as cutting the central box geometry. The housing sizes may differ for posterior stabilized and constrained type femoral components. The sizes may also differ from patient to patient and implant to implant. Therefore, a different amount of bone depth may need to be removed, depending upon the patient and the type of femoral implant that will be used.

For optimum results, range of motion, and patient comfort, it is important that the tibial and femoral components are properly aligned relative to the tibia and femur during implantation of the components. There are many accompanying instruments that are used to prepare the femur, e.g., cutting blocks, reamers, saws, chisels, and trial components.

Typically, the posterior bone removed from the distal femur to accommodate the cam housing discussed above is removed using a cutting block and collet configuration. One example is shown and described by U.S. Pat. No. 5,819,829, the entire contents of which are hereby incorporated by reference. The cutting block is placed on the patient's femur with bone spikes and used to make anterior/posterior chamfer cuts. A rotary reamer is then inserted through a collet in the block to prepare the femur for the cam housing (to cut the central box geometry). A box chisel can then be used to complete the preparation. All of this preparation is done using the cutting block as the reference guide.

Some problems encountered with the use of such a system are that once the surgeon has prepared the desired cuts in the femur, s/he will need to remove the cutting block and secure a femoral trial to the prepared distal femur in order to check the fit and sizing. This trialing step is important to ensure that the ultimate component that is implanted fits the area that has been prepared. If additional preparation for the area where the cam housing will fit needs to be done, the trial is removed, the cutting block is re-positioned (which often requires insertion of additional bone spikes) and the cuts are further perfected. It is possible that this procedure may need to be repeated more than once, causing undesired and additional bone removal or degradation during each repositioning step.

Moreover, when the bone is removed to receive the posterior stabilized and constrained femoral implant components through the cutting block, the surgeon does not have a "feel" for how the cuts relate to the actual implant because the cutting block is not shaped like the implant. It is essentially a square block.

Other systems have attempted to cut central box geometry through a femoral trial, but they have not used a constrained box geometry, which can be important to control the reaming instruments and to prevent damage to tissues that are not to be removed. If the trial being used a cutting guide does not have a posterior ledge or stopping portion, it is not always clear where the posterior cutting should stop. Moreover, such systems also fail to provide the desired adjustability that is needed in many cases. If the cutting guide is attached at only a single position with respect to the trial, the surgeon is limited to preparing the box geometry only where the cutting guide sits. See e.g., U.S. Pat. No. 4,721,104, the entire contents of which are hereby incorporated by reference.

Accordingly, there is a need in the art to provide a distal femoral trial that allows a surgeon to cut the central box geometry of a distal femur using an implant-shaped trial, while also providing removability and adjustability of the guide that controls the depth and direction of the cutting instruments. There is also a need for such systems that provide constrained box geometry. There is a further need for surgical methods and kits that use such a trial.

SUMMARY

Various embodiment of the present invention provide a distal femoral trial that allows a surgeon to cut the central box geometry of a distal femur using an implant-shaped trial. The trial includes a cutting guide that is removable from the trial and adjustable with respect to the trial. The guide is intended to control the depth and direction of the cutting instruments used to prepare the femur for a posterior stabilized implant.

DETAILED DESCRIPTION OF THE DRAWINGS

Figure 1:
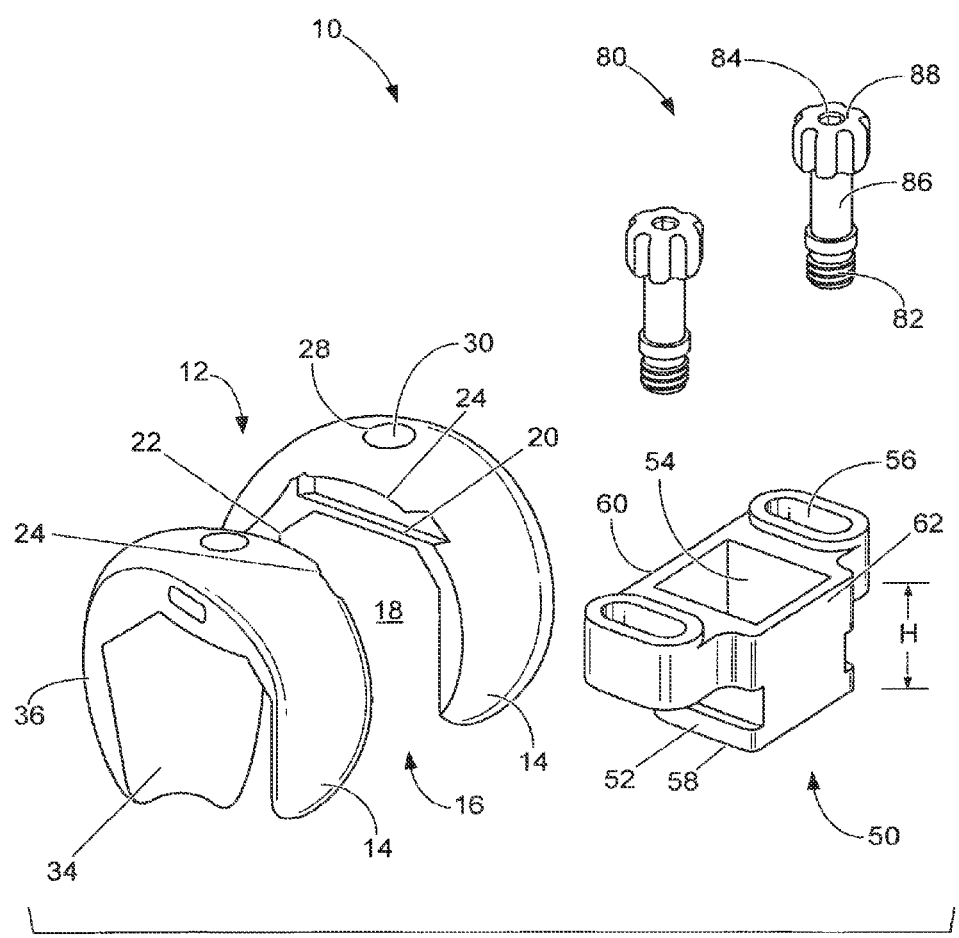
FIG. 1 shows an exploded perspective view of an assembly according to one embodiment of the invention.
Figure 7:
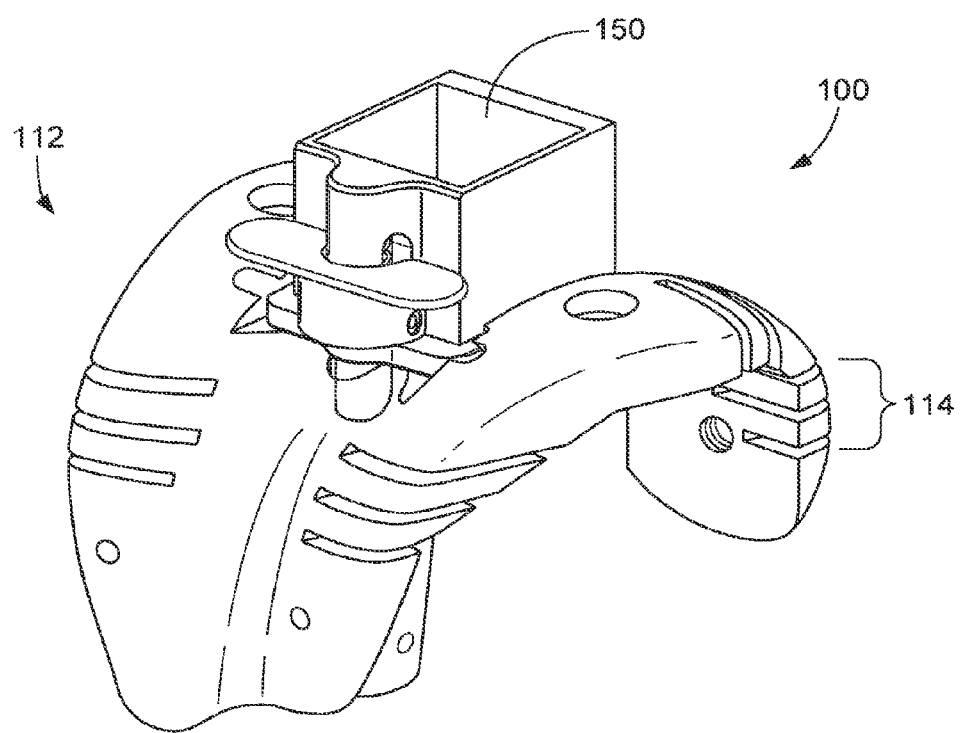
FIG. 7 shows the trial of FIG. 5 in combination with the cutting block of FIG. 6.

FIG. 1 shows a femoral trial component 12, a cutting guide 50, and retaining bolts 80, collectively referred to as assembly 10. FIG. 7 shows an alternate femoral trial component 112 and cutting guide 150, collectively referred to as assembly 100. In both embodiments, the trial 12, 112 is made with the same or similar proximal and anterior/posterior box geometry as the prosthesis that will be used so that it fits the geometry of the surface of the femur that has already been resected. It also has the same articulating surface as the prosthesis except that there is an opening to accommodate a cutting guide to prepare the central stabilizing/constraining box geometry. As shown in FIG. 7, the trial may also include various cutting slots 114, allowing the trial to also be used to prepare various resections on the femur. This feature is optional and although only shown with response to the embodiment shown in FIG. 8, may be used on any trial made according to various aspects of this invention.

Figure 3A:
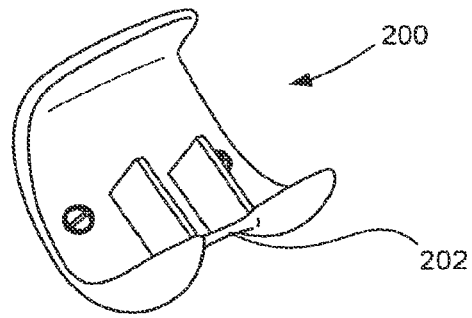
FIGS. 3A and 3B show an example of an implant that is to be received by the bone prepared using various embodiments of this invention.
Figure 3B:
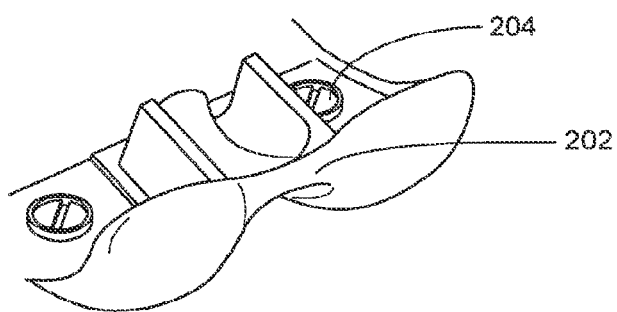

In a specific embodiment, the trial 12 has two condylar regions 14 and an anterior patellar region 34 with an articulating surface 36. The condylar regions 14 define an opening 16. This opening 16 is where the distal femur is prepared to receive an implant having a cam that cooperates with a tibial post. An example of the cam potion 202 of an actual implant 200 is shown in FIGS. 3A and 3B. The bone of the femur must be prepared to make room to receive this cam 202, and the opening 16 in trial 12 allows the space for instruments to pass during preparation.

The opening 16 defines a central portion 18 of the implant 12 that has an anterior-most portion 22 and opening side edges 24. In the particular embodiment shown, in FIGS. 1 and 2, the opening side edges 24 define orientation slots 20. Orientation slots 20 are adapted to receive base 52 of cutting guide 50. In the particular embodiment shown, cutting guide base 52 is defined by an outer flange 58. Edges of flange 52 may slide into orientation slots 20 to secure trial 12 and cutting guide 50 together.

Figure 2:
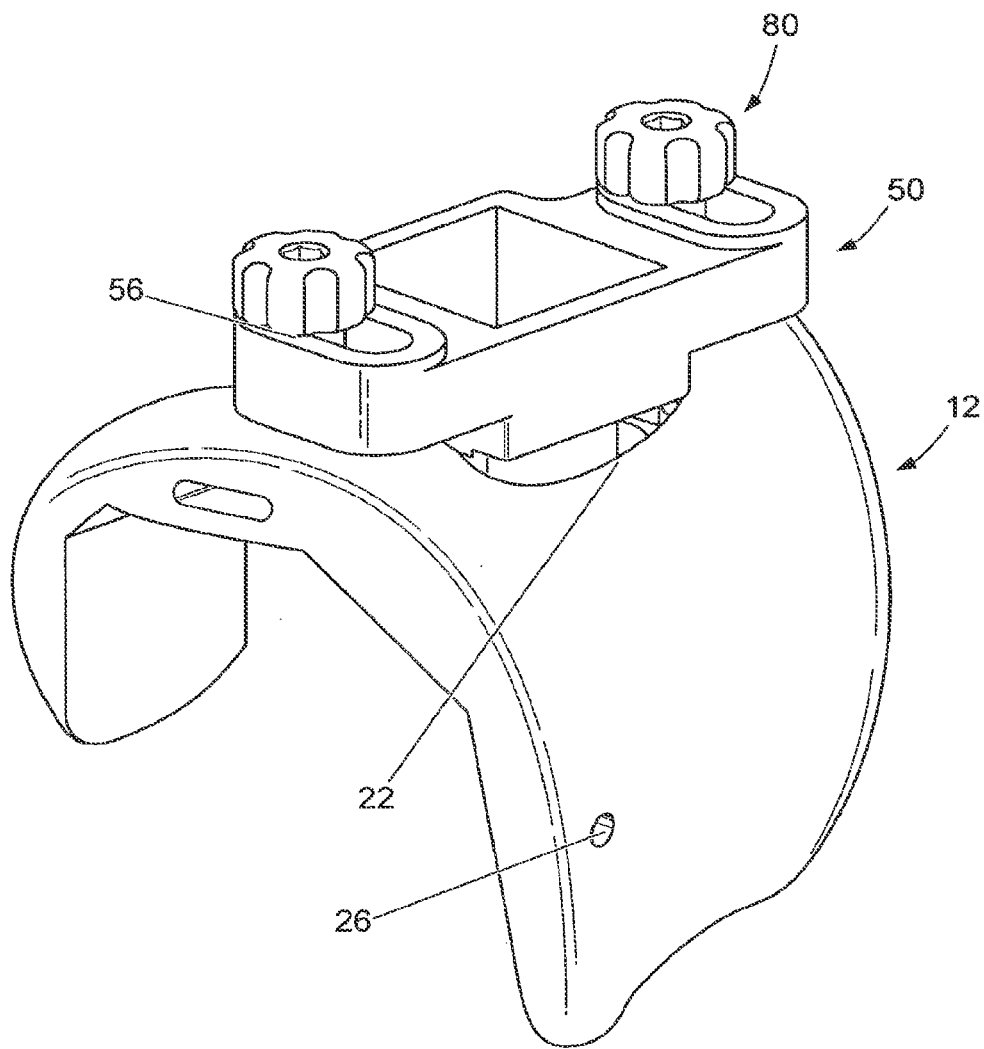
FIG. 2 shows the embodiment of FIG. 1 in an assembled position.

The trial 12 also features one or more fixation holes 26, an example of which is shown in FIG. 2. Fixation holes 26 are adapted to receive pins, screws, pegs, or another securing mechanism to secure trial 12 in place on the patient's bone.

In a particular embodiment, the trial 12 has receiving portions 28, which are adapted to receive bolts 80. Bolts 80 are intended to secure cutting guide 50 in place, explained in more detail below. Receiving portions 28 may or may not feature threads 30.

Another embodiment of trial 12 may have one or more slight indentations at the posterior end of the trial the provide stopping points to allow a post of cutting block to sit into as it is moved into position. For example, the indentation could receive a movable securing pin of the cutting guide that secures cutting guide in place with respect to trial 12 without the need to use bolts 80, the use of which are described in more detail below. Further connection mechanisms may be used also; the general concept is to provide a trial and a cutting block that are securable in a fixed position, but where that fixed position is adjustable before being secured.

Figure 5A:
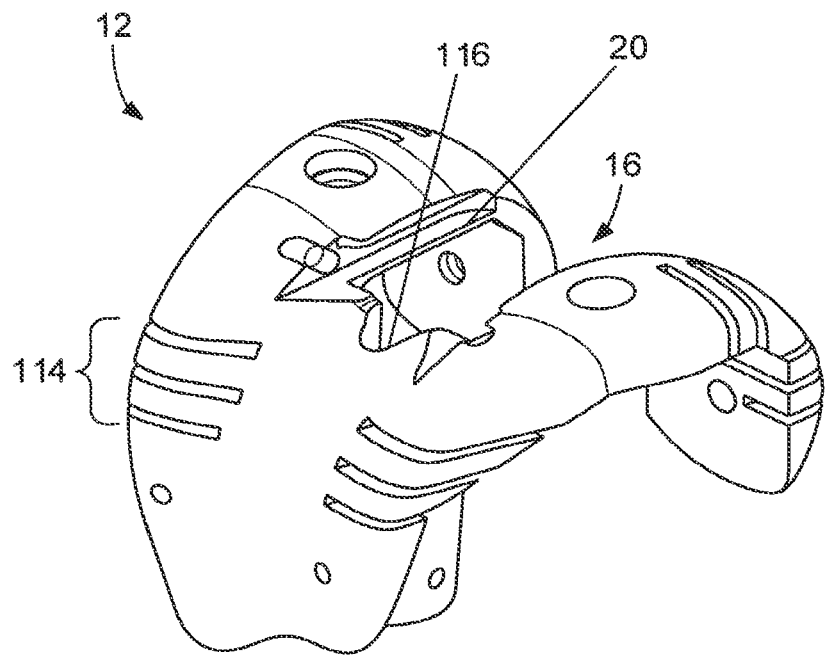
FIG. 5A shows a side perspective view of an alternate embodiment of a trial that may be used according to various embodiments of the invention.
Figure 5B:
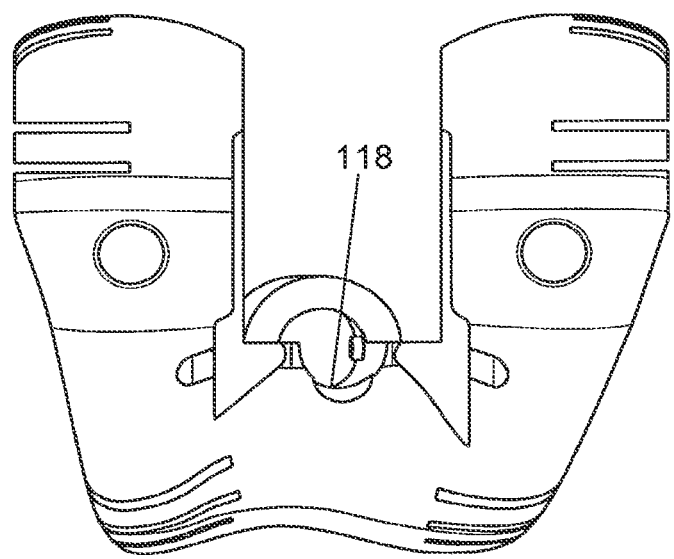
FIG. 5B shows a top plan view of an alternate embodiment of a trial.

A further embodiment of trial 112 is shown in FIGS. 5A and 5B. This trial 112 may be similar to trial 12 in that it has condylar regions and other similar features. In the particular embodiment shown, however, the trial 112 has an opening 16 with an anterior abutment portion 116 at its anterior-most portion. The anterior abutment portion 116 is intended to receive a corresponding anterior abutment pin 152 of cutting block 150, shown in FIG. 6. In use, member 154 is pulled up (in the direction of arrow "A"), which causes pin 152 to be pulled up in the same direction. This may be accomplished through the use of a spring and spring pin assembly or any other feature. If a spring and spring pin is used, the upward movement of member 154 compresses a spring 156 that rests on top of member 154 and is retained in the guide 150. When member 154 is released, spring 156 forces pin 152 to extend out of guide 150 to the extended position shown in FIG. 6.

In use, while member 154 is activated and pin 152 is retracted, the cutting block 150 is slid into place in the opening of trial 112 along orientation slots 20. When the proper position has been reached, the user releases member 154, causing pin 152 to extend from block 150. In some embodiments, pin 152 interfaces with abutment portion 116 of trial 112, as shown in FIG. 7. In even further and preferred embodiments shown in FIG. 5B, pin 152 may be received by pin receiving portion 118 to secure pin 152 (and cutting guide 150) in place. To remove guide 150 from trial 112, the member 154 is lifted back up and the guide can slide out of orientation slots 20. In a particularly preferred embodiment, the trial 112 may have a pin receiving portion 118, as shown in FIG. 5B. In a particular embodiment, pin receiving portion 118 captures the anterior portion of the pin, retaining the guide assembly from anterior dislocation while allowing posterior freedom to the posterior stop (or wall capture).

The reamer used typically is side cutting, so anterior/posterior resection is carried out until the cutter reaches both A/P stops. If the stops are positioned so that A/P freedom is not allowed, then side cutting or resecting in an NP direction is not needed. This depends on the size and design of the trial.

Figure 6:
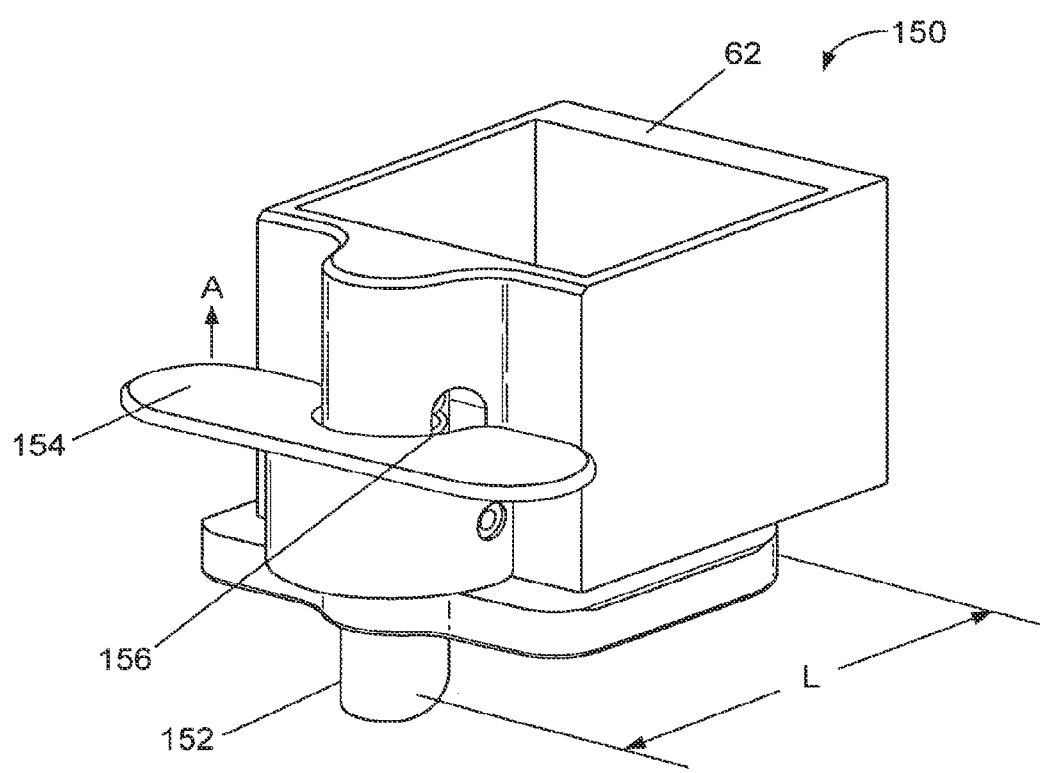
FIG. 6 shows a side perspective view of an alternate cutting block that may be used according to various embodiments of the invention.

The directional limits are controlled by the length L of the block 150, as shown by "L" in FIG. 6. The shorter the length of block 150, the more anterior/posterior movement will be allowed in orientation slots 20.

It is not required that the block 50, 150 cooperate with the trial with orientation slots 20. It should be understood that the block 50 may snap into place or otherwise be attached to trial through other means.

The cutting guide 50, 150 is preferably a box-shaped component that is intended to guide instruments during the preparation of the femur. The box is preferably formed by four complete vertical sides, but it is possible for the box to have fewer sides and sides that are of different heights and lengths. (The term "box" is used for convenience only, and is intended to refer to a cutting guide configuration.) In a particularly preferred embodiment, guide has a posterior wall or capture 62 that acts to constrain posterior cutting.

Figure 4:
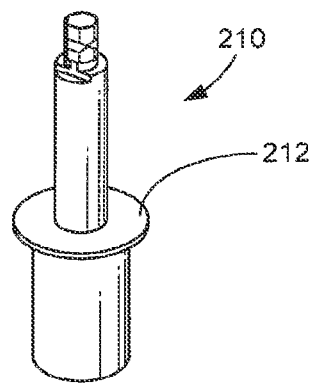
FIG. 4 shows an example of a reamer that may be used to prepare a patient's bone in connection with various embodiments of the assemblies described herein.

Cutting guide 50, 150 is intended to be attached to (and removable from) the trial 12, 112 during the preparation of the internal box geometry phase of the surgery. The guide 50, 150 has an internal box 54 that accepts a reamer, as example of which is shown in FIG. 4. The height H of internal box may vary. In addition, the width and other dimensions may be varied as well to allow the guide 50 to be fitted and femoral size specific, accommodating various box geometry depths and anterior/posterior lengths.

In preferred embodiments, more than one guide 50, 150 is provided to accommodate various implant and patient sizes. The box geometry depths are controlled by the height of the guide 50. As shown in FIG. 4, an example of a reamer 210 that may be used with guide 50 has a collar 212 that determines how deep the reamer can extend into bone. The collar 112 is stopped by the top surface 60 of guide 50. Thus, providing variously-sized guides 50 with different heights allows the surgeon to prepare cavities of different depths, while using the same reamer 110.

In the embodiment shown in FIG. 7, the NP direction is controlled by the length of guide 150. In the alternate embodiment shown in FIGS. 1 and 2, the NP direction is controlled by directional limit slots 56. These slots 56 are adapted to receive bolts 80, if used. The medial/lateral location of slots 56 is such that the slots 56 fit the prosthetic lug punch hole locations 104 (shown in FIG. 3B). The slots 56 also allow guide 50 to be positioned in any desirable anterior/posterior position on the trial 12 so that it correlates with the position and length of the stabilizing/constraining box geometry needed for the desired prosthetic size. Slots 56 are adapted to receive bolts, as shown in FIG. 2, in order to secure guide 50 in place.

This feature allows the surgeon to position the trial 12 as needed in the medial/lateral position, and the position guide as needed in the anterior/posterior direction, giving the surgeon a clear view of the cuts to be made with respect to the shape and position of the ultimate implant to be used. The bolts 80 limit the anterior/posterior movement once the guide 50 is properly placed.

The retaining bolts 80, shown in FIGS. 1 and 2 have posts 86 with heads 88 at one end and optional threads 82 at the other end. In a preferred embodiment, the bolts 80 are cannulated 84 to allow additional fixation pins to be used to further secure to the guide 50 and bolts 80 to the patient's distal femur. If threads 82 are provided, they may cooperate with threads 30 of receiving portions 28. In a particularly preferred embodiment, bolt heads 88 are broached to allow for the use of a hex driver.

Another way that the NP distance that block is allowed to travel with respect to trial can be controlled is to insert bone spikes or screws directly into the distal bone, through the directional limit slots without the use of bolts 80 or through any other area of the trial, which would secure the assembly and eliminate the need to use bolts as A/P translation stops. An alternate embodiment would be to insert bone spikes or screw through cannulated bolts 80.

During surgery, the trial 12, 112 is placed on the distal femur after preparatory resections have been made to accommodate a distal-femoral prosthesis without a stabilizing/constraining, median box. Such cuts and methods for preparing the distal femur are known in the art. The trial 12, 112 is then positioned (via bone coverage and/or trialing with the tibia and/or patella) in the desired medial/lateral position and pinned in place through one or more fixation holes 26. In a preferred embodiment, at least one fixation hole 26 is located on the patellar region 34 (or anterior flange).

The cutting guide 50, 150 is then placed in the orientation slots 20 on opening side edges 24 of trial 12. If necessary, retaining bolts 80 are then threaded into receiving portions 28 in the trial 12. Bolts 80 can be tightened by a knob-style head or with a hex driver to the desired resistance. The cutting guide 50 can be tightened in any given place along the orientation slots 20 and along the directional-limit slots 56 with the retaining bolts 80, if desired. If additional fixation is desired, bone spikes or other securing mechanisms can be placed through the cannulation area 84 of bolts 80 and into the distal femur. Once the bone resections through the cutting guide 50, 150 are preformed using known methods, the cutting guide 50, 150 is then removed from the trial 12, while the trial 12 stays in place on the patient's femur. Any necessary trial verification may be performed before removing the trial 12. If additional box geometry preparation is needed, the cutting guide 50, 150 can be replaced into position, without having to re-secure it to bone, which helps prevent any bone degradation and deterioration caused by the surgery and the need to re-cut or re-position.

Changes and modifications, additions and deletions may be made to the structures and methods recited above and shown in the drawings without departing from the scope or spirit of the invention and the following claims.

What is claimed is:

1. A method of knee arthroplasty, comprising:
   (a) resecting a patient's distal femur with anterior and posterior cuts;
   (b) positioning a femoral trial component on the distal femur, the trial component comprising (i) condylar regions separated by an opening and (ii) a removable cutting guide adapted to be secured in a fixed relationship with the opening while at any of multiple anterior/posterior locations along the condylar regions;
   (c) securing the removable cutting guide in a fixed relationship relative to the opening;
   (d) after securing the removable cutting guide in the fixed relationship relative to the opening, preparing the patient's distal femur using the removable cutting guide to guide at least one cutting instrument; and
   (e) controlling the at least one cutting instrument using the removable cutting guide.

2. The method of claim 1, further comprising implanting an implant on the distal femur after controlling the at least one cutting instrument.

3. The method of claim 2, wherein implanting the implant comprises implanting an implant having a cam configured to cooperate with a tibial post.

4. The method of claim 1, further comprising adjusting a guide surface in an anterior or posterior direction.

5. The method of claim 1, further comprising adjusting a guide opening in an anterior or posterior direction.

6. The method of claim 1, further comprising pinning the femoral trial component in place.

7. The method of claim 1, further comprising threading at least one retaining bolt into a receiving portion of the femoral trial component.

8. The method of claim 1, further comprising placing at least one bone spike through the femoral trial component.

9. The method of claim 1, further comprising removing the removable cutting guide from the femoral trial component, verifying additional preparation is needed without removing the femoral trial component, and replacing the removable cutting guide in substantially the same prior position.

10. The method of claim 1, wherein positioning the femoral trial component comprises positioning a trial component comprising a removable cutting guide having a rectangular box shape and an internal rectangular box that accepts the at least one cutting instrument; and
wherein preparing the patient's distal femur comprises preparing a box geometry of the patient's distal femur to receive a prosthesis using the internal rectangular box of the removable cutting guide to guide the at least one cutting instrument.

11. The method of claim 10, wherein controlling the at least one cutting instrument comprises controlling a depth of the box geometry.

12. The method of claim 11, wherein controlling the depth of the box geometry comprises controlling the depth of the box geometry according to a length of the removable cutting guide.

13. A method of knee arthroplasty, comprising:
(a) resecting a patient's distal femur with anterior and posterior cuts;
(b) positioning a femoral trial component on the distal femur, the trial component comprising condylar regions separated by an opening;
(c) engaging a removable cutting guide with the femoral trial component, the removable cutting guide being adapted to be secured at different anterior/posterior locations relative to the trial component;
(d) positioning the removable cutting guide relative to the opening; and
(e) securing the removable cutting guide in a fixed relationship relative to the opening and prior to cutting using the removable cutting guide.

14. The method of claim 13, further comprising preparing the patient's distal femur to receive a prosthesis using the removable cutting guide to guide cutting instruments.

15. The method of claim 14, further comprising implanting an implant on the prepared distal femur.

16. The method of claim 15, wherein implanting the implant comprises implanting an implant having a cam configured to cooperate with a tibial post.

17. The method of claim 13, further comprising translating a guide surface or a guide opening of the removable cutting guide in an anterior or posterior direction while the removable cutting guide is engaged with the femoral trial component.

18. The method of claim 13, wherein positioning the femoral trial component comprises positioning a trial component in which the opening that separates the condylar regions defines a central portion with an anterior-most portion and opening side edges.

19. The method of claim 13, further comprising adjusting the removable cutting guide in an anterior or posterior direction prior to securing the removable cutting guide.

20. The method of claim 19, wherein adjusting the removable cutting guide in an anterior or posterior direction comprises positioning the removable cutting guide using directional limit slots to achieve a desired anterior/posterior position on the femoral trial component.

21. The method of claim 13, further comprising inserting a portion of the removable cutting guide into the opening prior to securing the removable cutting guide.

22. The method of claim 13, wherein engaging the removable cutting guide with the femoral trial component comprises sliding the removable cutting guide into place along orientation slots.

23. The method of claim 13, further comprising preparing the patient's distal femur to receive a prosthesis using the removable cutting guide to guide cutting instruments and moving a reamer between an anterior stop and a posterior stop within an internal box geometry.

24. The method of claim 13, wherein the femoral trial component has a plurality of stopping points, and wherein securing the removable cutting guide comprises moving a securing pin into a portion of at least one of the plurality of stopping points.

25. The method of claim 13, further comprising removing the removable cutting guide from the femoral trial component, verifying additional preparation is needed without removing the femoral trial component, and replacing the removable cutting guide in substantially the same prior position.

26. The method of claim 13, wherein the femoral trial component opening has an anterior abutment portion, and wherein the method further comprises releasing an anterior abutment pin of the cutting guide such that the pin engages the anterior abutment portion.

27. A method of facilitating knee arthroplasty, comprising:
(a) resecting a patient's distal femur with anterior and posterior cuts;
(b) positioning a femoral trial component on the distal femur, the trial component comprising condylar regions separated by an opening;
(c) selecting at least one removable cutting guide from a plurality of removable cutting guides, each of the plurality of removable cutting guides having a different length;
(d) positioning the at least one removable cutting guide relative to the opening, the at least one removable cutting guide being adapted to be secured at different anterior/posterior locations relative to the trial component; and
(e) securing the at least one removable cutting guide in a fixed relationship relative to the opening prior to cutting using the at least one removable cutting guide.

28. The method of claim 27, further comprising:
preparing the patient's distal femur to receive a prosthesis using the at least one removable cutting guide to guide cutting instruments;
implanting a prosthesis on the prepared distal femur.

29. The method of claim 27, further comprising adjusting a guide surface or a guide opening in an anterior or posterior direction.

30. The method of claim 27, further comprising pinning the femoral trial component in place.

31. The method of claim 27, further comprising removing the at least one removable cutting guide from the femoral trial component, verifying additional preparation is needed without removing the femoral trial component, and replacing the at least one removable cutting guide in substantially the same prior position.

32. The method of claim 27, wherein positioning the femoral trial component comprises positioning a trial component in which the opening that separates the condylar regions defines a central portion with an anterior-most portion and opening side edges.

33. A method of knee arthroplasty, comprising:
(a) resecting a patient's distal femur with anterior and posterior cuts;
(b) positioning a femoral trial component on the distal femur, the trial component comprising condylar regions separated by an opening, the opening defining a central portion with an anterior-most portion;

(c) positioning a removable cutting guide relative to the opening, the removable cutting guide being adapted to be secured at different anterior/posterior locations relative to the trial component;

(d) placing at least one bone spike through the femoral trial component; and (e) securing the removable cutting guide in a fixed relationship relative to the opening.

34. The method of claim 33, further comprising preparing the patient's distal femur to receive a prosthesis using the removable cutting guide to guide cutting instruments while the removable cutting guide is in the fixed relationship relative to the opening.

35. The method of claim 33, further comprising implanting a prosthesis on the distal femur.

36. The method of claim 33, further comprising adjusting a guide surface or a guide opening in an anterior or posterior direction.

37. The method of claim 33, further comprising inserting a portion of the removable cutting guide into the opening prior to securing the removable cutting guide.

38. The method of claim 33, further comprising threading at least one retaining bolt into a receiving portion of the femoral trial component.

39. The method of claim 33, wherein positioning the femoral trial component comprises positioning a trial component in which the opening that separates the condylar regions defines a central portion with an anterior-most portion and opening side edges.

40. The method of claim 1, wherein securing the removable cutting guide in the fixed relationship relative to the opening comprises securing the removable cutting guide with at least a portion of the removable cutting guide extending into the opening.

41. The method of claim 14, wherein positioning the femoral trial component on the distal femur comprises positioning a femoral trial component in which each of the condylar regions includes a curved articulating surface; and wherein securing the removable cutting guide in the fixed relationship relative to the opening comprises securing the removable cutting guide with at least a portion of the removable cutting guide located between the opening between the curved articulating surfaces.

42. The method of claim 1, wherein securing the removable cutting guide in the fixed relationship relative to the opening comprises securing the removable cutting guide such that the removable cutting guide provides an anterior stop and a posterior stop for movement of the at least one cutting instrument.

* * * * *

UNITED STATES PATENT AND TRADEMARK OFFICE
CERTIFICATE OF CORRECTION

PATENT NO. : 9,649,205 B2
APPLICATION NO. : 14/725693
DATED : May 16, 2017
INVENTOR(S) : Roger Ryan Dees, Jr.

Page 1 of 1

It is certified that error appears in the above-identified patent and that said Letters Patent is hereby corrected as shown below:

In the Claims

At Column 10, Line 9 (Claim 41), replace "claim 14" with --claim 1--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*